(12) United States Patent
Roedersheimer

(10) Patent No.: US 9,402,881 B2
(45) Date of Patent: Aug. 2, 2016

(54) TISSUE REGENERATION AND WOUND TREATMENT METHODS WITH PLATELET DERIVED COMPOSITIONS

(71) Applicant: Mark T. Roedersheimer, Aurora, CO (US)

(72) Inventor: Mark T. Roedersheimer, Aurora, CO (US)

(73) Assignee: The Regents of the University of Colorado, a body corporate, Denver, CO (US)

( * ) Notice: Subject to any disclaimer, the term of this patent is extended or adjusted under 35 U.S.C. 154(b) by 0 days.

(21) Appl. No.: 14/603,504

(22) Filed: Jan. 23, 2015

(65) Prior Publication Data

US 2015/0150942 A1    Jun. 4, 2015

Related U.S. Application Data

(63) Continuation of application No. 13/645,525, filed on Oct. 5, 2012, now abandoned, which is a continuation of application No. 12/682,782, filed as application No. PCT/US2008/080053 on Oct. 15, 2008, now Pat. No. 8,282,963.

(60) Provisional application No. 60/980,159, filed on Oct. 15, 2007.

(51) Int. Cl.

| *A61K 38/18* | (2006.01) |
|---|---|
| *A61K 35/19* | (2015.01) |
| *A61L 15/40* | (2006.01) |
| *A61L 26/00* | (2006.01) |
| *A61L 27/36* | (2006.01) |
| *A61L 27/60* | (2006.01) |
| *C07K 14/475* | (2006.01) |

(52) U.S. Cl.
CPC ............ *A61K 38/1866* (2013.01); *A61K 35/19* (2013.01); *A61K 38/1808* (2013.01); *A61K 38/1841* (2013.01); *A61K 38/1858* (2013.01); *A61L 15/40* (2013.01); *A61L 26/0057* (2013.01); *A61L 27/3616* (2013.01); *A61L 27/60* (2013.01); *C07K 14/475* (2013.01)

(58) Field of Classification Search
None
See application file for complete search history.

(56) References Cited

U.S. PATENT DOCUMENTS

| 4,418,691 | A | * | 12/1983 | Yannas | A61L 27/60 424/548 |
|---|---|---|---|---|---|
| 4,874,746 | A | * | 10/1989 | Antoniades | A61K 38/1841 514/8.2 |
| 5,034,375 | A | * | 7/1991 | Antoniades | A61K 38/1808 514/7.6 |
| 5,149,691 | A | * | 9/1992 | Rutherford | A61K 38/1858 424/484 |
| 5,447,725 | A | * | 9/1995 | Damani | A61K 9/0063 424/426 |
| 5,599,558 | A | * | 2/1997 | Gordinier | A61K 35/16 424/520 |
| 5,651,966 | A | * | 7/1997 | Read | A01N 1/0221 424/532 |
| 5,770,228 | A | * | 6/1998 | Edwards | A61K 9/0014 424/488 |
| 6,328,765 | B1 | * | 12/2001 | Hardwick | A61F 2/2803 623/23.58 |
| 6,627,215 | B1 | * | 9/2003 | Dale | A01N 57/16 424/443 |
| 6,732,738 | B1 | * | 5/2004 | Komeda | A61K 38/1825 128/898 |
| 2006/0039991 | A1 | * | 2/2006 | Barrueta | A61K 35/16 424/530 |

FOREIGN PATENT DOCUMENTS

WO    WO 91/13905    *   9/1991    ............... C07K 3/12

OTHER PUBLICATIONS

Valeri et al.—Release of platelet-derived growth factors and proliferation of fibroblasts in the releasates from platelets stored in the liquid state at 22° C. after stimulation with agonists—Transfusion, 46, 225-229, 2006.*

Pietromaggiori et al.—Freeze-dried platelet-rich plasma shows beneficial healing properties in chronic wounds—Wound repair and regeneration, 14, 573-580, 2006.*

* cited by examiner

*Primary Examiner* — Elly-Gerald Stoica

(74) *Attorney, Agent, or Firm* — Don D. Cha; Hamilton DeSanctis & Cha, LLP

(57) ABSTRACT

This invention provides methods for extracting platelets, compositions obtained therefore, and methods for using the same.

10 Claims, 2 Drawing Sheets

TISSUE REGENERATION AND WOUND TREATMENT METHODS WITH PLATELET DERIVED COMPOSITIONS

CROSS-REFERENCE TO RELATED APPLICATIONS

This is a continuation of U.S. patent application Ser. No. 13/645,525, filed Oct. 5, 2012, which is a continuation of U.S. patent application Ser. No. 12/682,782, filed Apr. 13, 2010, now U.S. Pat. No. 8,282,963, issued Oct. 9, 2012, which is a §371 U.S. National Stage entry from PCT Patent Application No. PCT/US08/80053, filed Oct. 15, 2008, which claims the priority benefit of U.S. Provisional Application No. 60/980,159, filed Oct. 15, 2007, which is incorporated herein by reference in its entirety.

STATEMENT REGARDING FEDERALLY FUNDED RESEARCH

This invention was made with government support under contract number HL007171 awarded by the National Institutes of Health. The government has certain rights in the invention.

FIELD OF THE INVENTION

The present invention relates to methods for extracting platelets, compositions obtained therefrom, and methods for using the same.

BACKGROUND OF THE INVENTION

New blood vessel formation, or angiogenesis, is requirement for the repair and regeneration of damaged body tissues. This process requires the coordinated activity of multiple cell types including endothelial cells, smooth muscle and other mesenchymal cells, as well as cells of the monocyte/macrophage lineage. A great amount of work has been put into identifying growth factors that can stimulate angiogenesis for therapeutic purposes. Much attention has been focused on the molecule VEGF (vascular endothelial growth factor) because of its central role in the process.

VEGF is believed to be a very specific stimulator of endothelial cells that line the interior of blood vessels. Augmentation of motility, mitogenesis, and differentiation of endothelial cells can be demonstrated in response to VEGF readily in cell culture. In addition, it has been shown that animals lacking the gene for VEGF die early in development from a failure of blood vessel formation. Thus, it is believed that VEGF could be used for therapeutic purposes to stimulate angiogenesis, for example, in treatment of heart disease and peripheral vascular insufficiency. However, it has been shown that in some instances delivery of VEGF to ischemic tissue leads to the formation of very weak, leaky blood vessels lacking the support needed from the other cell types. In these instances, VEGF alone was not able to stimulate the formation of entire mature, therapeutically valuable, blood vessels. Without being bound by any theory, it is believed that a single growth factor alone is not sufficient to stimulate the coordinated activity of all of the necessary cell types to bring about angiogenesis for therapeutic purposes, e.g., in wound healing.

Wound healing is a complex cascade of cellular and biochemical events which lead to wound closure and repair of tissues. Conventionally, three successive phases are classically distinguished in the wound healing process: (1) the inflammatory phase, which corresponds to increased vascular permeability and migration of leukocytes and macrophages; (2) the proliferative phase, characterized by, among others, fibroblast proliferation and collagen synthesis resulting in granulation tissue formation; and (3) the remodeling phase where collagen and granulation tissue rearrangements result in scar resorption.

One of the first events which usually occurs in a wound is blood extravasation that results in platelet aggregation and impregnation of the wound with platelet and serum constituents. Among these constituents are polypeptide growth factors, which are known to play a major role in tissue regeneration. It has been shown that platelet a granules, which are released by aggregated platelets, are one of the richest physiological source of platelet-derived growth factor (PDGF) and transforming growth factor-$\beta$ (TGF-$\beta$), while serum contains high amounts of insulin-like growth factor I (IGF-I), IGF-II and their binding proteins (IGF-BPs).

PDGFs include PDGF, platelet derived angiogenesis factor (PDAF), TGF-$\beta$ and platelet factor-4 (PF-4), which is believed to be a chemoattractant for neutrophils. PDGF is a mitogen and chemoattractant for fibroblasts and smooth muscle cells and is a stimulator of protein synthesis in cells of mesenchymal origin, including fibroblasts and smooth muscle cells. PDGF is also a nonmitogenic chemoattractant for endothelial cells.

TGF-$\beta$ is a chemoattractant for macrophages and monocytes. Depending on the presence or absence of other growth factors, TGF-$\beta$ increases the tensile strength of healing dermal wounds. TGF-$\beta$ also inhibits endothelial cell mitosis, and stimulates collagen and glycosaminoglycan synthesis by fibroblasts.

Other growth factors, such as epidermal growth factor (EGF), TGF-$\alpha$, and heparin binding growth factors (HBGFs) such as VEGF and fibroblast growth factor (FGF) and osteogenin, are also believed to be involved in wound healing. Epidermal growth factor, which is found in gastric secretions and saliva, and TGF-$\alpha$, which is made by both normal and transformed cells, are structurally related and may recognize the same receptors that mediate cell proliferation on epithelial cells. It is believed that both factors are involved in accelerating re-epithelialization of skin wounds.

The in vivo mode of action of these growth factors involves chemoattraction at the wound site, cell proliferation, and collagen synthesis. One very-interesting feature of these products is that it has been shown that some of them, for example, PDGF and IGFs, work synergistically in stimulating wound repair.

Growth factors are, therefore, potentially useful for specifically promoting wound healing and tissue repair. The addition of exogenous growth factors to a wound has been shown to increase the rate at which the wound is closed, the number of cells in the healing area, the growth of blood vessels, the total rate of deposition of collagen, and strength of the scar.

Platelets are fragments of cells that circulate in the blood and participate in the early phases of wound healing by binding to damaged tissue and releasing a large variety of factors that begin and sustain the healing process. Numerous factors, including VEGF, are known to be present in platelets that have a role in blood vessel formation making them a good source to look for therapeutically valuable mixtures. A number of studies have been done to show that isolates of growth factors from platelets can enhance the healing of dermal wounds. In addition, surgeons in a number of areas routinely harvest and concentrate platelets from the blood of patients (PRP, platelet-rich plasma) as a source of growth factors to be placed into specific areas of the body in need of tissue regeneration.

Platelet-derived wound healing formulae (PDWHF) are known. For example, a platelet extract, which is in the form of a salve or ointment for topical application, has been used by others in an attempt to facilitate wound healing. Unfortunately, most conventional PDWHFs are obtained by centrifuging whole blood to obtain a plasma rich in platelets but free of red blood cells and treating the platelet rich plasma with thrombin to stimulate the production of a releasate, which can be combined with collagen. These PDWHFs typically have a limited concentration of growth factors with high concentration of albumin (e.g., 9.9%). Accordingly, clinical utility of these conventional PDWHFs are limited. In addition, these PDWHFs typically contain essentially non-mature growth factors due to the use of thrombin in obtaining PDWHFs. Furthermore, conventional PDWHF production is relatively expensive, thereby making the cost-benefit ratio of conventional PDWHFs questionable.

Revised sentence: Unfortunately, most conventional PDWHFs are obtained by centrifuging whole blood to obtain a plasma rich in platelets but free of red blood cells and treating the platelet rich plasma them with thrombin to stimulate the production of a releasate, which can be combined with collagen Autologous human platelet derived wound healing formula, made of thrombin activated platelet a granules, has also been shown to induce the healing of chronic ulcers, thus making growth factor extracts an advantageous alternative to the use of recombinant growth factors.

Accordingly, there is a continuing need for better wound healing compositions and methods for obtaining such compositions.

SUMMARY OF THE INVENTION

The present invention provides various platelet extract compositions that are useful in treating a wound, and promoting angiogenesis and/or tissue regeneration; methods and processes for producing the same from platelets; and methods for using the same.

Some aspects of the invention provide compositions comprising a growth factor, an angiogenesis activity, a tissue regenerative activity, or a combination thereof. Some compositions of the invention are produced by a process comprising:
  disrupting pelletized platelets in an extraction solution to produce an insoluble material portion and the extraction solution comprising a growth factor; and
  removing insoluble materials and proteins having molecular weight of 2 kD or less from said extraction solution to produce a composition comprising a growth factor.

The extraction solution can comprise ethanol, water, HCl, urea, guanidine, Phosphate buffer, NaCl, CaCl2, Arginine, Tris buffer, or a mixture thereof. However, it should be appreciated that other solvents and/or compounds can also be present in the extraction solution depending on particular needs.

In some embodiments, methods for disrupting pelletized platelets comprise sonication, homogenization, nitrogen cavitation, a French pressure cell, or a combination thereof.

Yet in other embodiments, the step of removing insoluble materials and proteins comprises:
  (i) filtering said extraction solution using an ultrafiltration process to remove insoluble materials and proteins having molecular weight of 2 kD or less; or
  (ii) removing insoluble materials from said extraction solution; and
    (a) dialyzing said extraction solution against an acidic solution using a semipermeable membrane having 2 kD or less MWCO; or
    (b) filtering said extraction solution using an ultrafiltration process to remove proteins having molecular weight of 2 kD or less.

Within these embodiments, in some instances, the step of dialyzing comprises using a semipermeable membrane having 8 kD or less MWCO.

Still in other embodiments, the process further comprises subjecting the extraction solution to an ultrafiltration process to remove any microorganisms that maybe present. Within these embodiments, in some instances the process further comprises lyophilizing the extraction solution to produce a solid composition comprising the growth factor. In some cases, the process further comprises dissolving the solid composition in a solution to produce a fluid composition comprising the growth factor.

In other embodiments, compositions of the invention comprise VEGF, TGF-β1, TGF-β2, PDGF-BB, EGF, or a mixture thereof.

Other aspects of the invention provide a wound healing composition comprising therapeutically effective amount of a composition of the invention and a pharmaceutically acceptable carrier.

In some embodiments, the pharmaceutically acceptable carrier comprises a bandage. In other embodiments, the pharmaceutically acceptable carrier comprises a pharmaceutically acceptable polymer.

Still other aspects of the invention provide methods for regenerating a tissue or treating a wound comprising contacting a desired site for tissue regeneration or the wound with an angiogenic composition comprising a composition of the invention.

In some embodiments, the desired site for tissue regeneration comprises a burn site, a graft donor site, an oral and maxillofacial surgery site, a mucogingival surgery site, a perioplastic surgery site, an oral mucosa site, or a combination thereof.

Yet other aspects of the invention provide methods for reducing the risk of microbial infection in a wound comprising treating the wound with a wound treatment composition comprising a composition of the invention.

Some aspects of the invention provide processes for producing a platelet extract having an angiogenic activity. Such methods typically comprise:
  disrupting pelletized platelets in an extraction solution to produce an insoluble material portion and the extraction solution comprising a growth factor; and
  removing insoluble materials and proteins having molecular weight of 2 kD or less from the extraction solution to produce a platelet extract having an angiogenic activity.

In some embodiments, methods for disrupting pelletized platelets comprise sonication, homogenization, nitrogen cavitation, a French pressure cell, or a combination thereof.

Yet in other embodiments, the step of removing insoluble materials and proteins comprises:
  (i) filtering the extraction solution using an ultrafiltration process to remove insoluble materials and proteins having molecular weight of 2 kD or less; or
  (ii) removing insoluble materials from the extraction solution; and
    (a) dialyzing the extraction solution against an acidic solution using a semipermeable membrane having 2 kD or less MWCO; or (b) filtering the extraction solution using an ultrafiltration process to remove proteins having molecular weight of 2 kD or less.

Within these embodiments, the step of dialyzing comprises using a semipermeable membrane having 8 kD or less MWCO.

Still in other embodiments, the process further comprises subjecting the platelet extract to an ultrafiltration process to remove any microorganisms that maybe present.

Yet in other embodiments, some processes of the invention further comprise lyophilizing the platelet extract to produce a solid platelet extract. Within these embodiments, in some instances processes of the invention further comprise dissolving the solid platelet extract in a solution to produce a platelet extract solution.

Some applications for compositions of the invention include treating burns of all kinds, and treating the wound that is created from the graft site when skin is taken from one site to be grafted onto a burn; all dental applications, in particular oral and maxillofacial applications including, without limitation, bone grafting, guided tissue regeneration, involving, without limitation, the maxillo (upper jaw) or mandible (lower jaw), tissue regeneration, mucogingival surgery, perioplastic surgery, or other regenerative tissues including, without limitation, the oral mucosa. Compositions of the invention can also be used in ENT applications; orthopedic wound healing applications, in particular joint replacement and tendon-bone graft; in surgical closures, in particular plastic surgery for scar reduction; treating battlefield wounds; in cardiovascular applications (in particular myocardial infarction); and chronic non-healing skin ulcers (e.g., especially prevalent in diabetics).

Other uses include treating external wounds. In addition to external wounds discussed above, exemplary external wounds that can be treated by compositions and processes of the invention include, but are not limited to, cuts (including surgical cuts or incisions), diabetic neuropathic ulcers, pressure ulcers (e.g., bed sores), regions of gingival recession undergoing surgical reconstruction, and any other external injuries that break tissues or skin.

Compositions and processes of the invention can also be used to treat internal wounds. For example, compositions and processes of the invention can be used to treat cardiovascular disease, peripheral vascular insufficiency, spinal cord injuries, gastrointestinal injuries (e.g., wounds resulting from ulcers), hepatic injuries, and any other injuries that require tissue regeneration and/or angiogenesis.

In one particular embodiment, compositions and processes of the invention are used to facilitate healing dental or oral wounds. For example, compositions and processes of the invention can be used to facilitate wounds from oral surgery, tooth extraction, tooth replacement, tooth implants, etc.

DETAILED DESCRIPTION OF THE INVENTION

Definitions

Figures 1A, 1B:
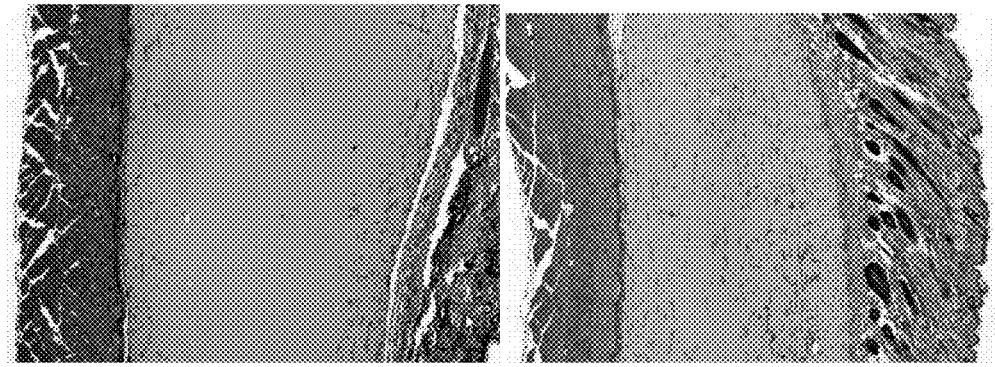
FIGS. 1A and 1B are magnified views of the cross-section of a Matrigel plug without and with the composition of the invention, respectively.

The term "pelletized platelets" refers to platelets that have been concentrated (e.g., by centrifugation or filtration) such that the bulk (typically 90%, often 95%, and more often 98%) of the natural media (e.g., serum, plasma, anticoagulant solution) in which the platelets are naturally found in have been removed.

When referring to platelets, the term "disrupted" means membranes of platelet cells and granules have been destroyed such that the contents are released.

"Low molecular weight proteins" refers to proteins having a molecular weight of 10 kD or less, typically 8 kD or less, and often 2 kD or less.

"Ultrafiltration" refers to a filtration process that removes microorganisms such as bacteria and/or virus. Typically, ultrafiltration is a membrane filtration in which hydrostatic pressure forces a liquid against a semipermeable membrane. Suspended solids, solutes of high molecular weight, and microorganisms are retained, while water and low molecular weight solutes pass through the membrane. This separation process is used in industry and research for purifying and concentrating macromolecular ($10^3$-$10^6$ Da) solutions, especially protein solutions.

A "pharmaceutically acceptable carrier" refers to any material or means that is used to deliver, transport, release, apply, or otherwise place a product or a composition of the invention to a desired or affected site. Exemplary pharmaceutically acceptable carriers include, but are not limited to, polymers (including binders, slow release polymer formulations, polymers used as an artificial skin, and other pharmaceutically acceptable polymers), bandages (including fabric bandages, polymeric bandages, and other solid materials that are used to treat wounds), solutions (such as those used in elixir, solutions used in intravenous administrations, and other pharmaceutically acceptable liquids), as well as all known materials that are used in treating wounds.

"Pharmaceutically acceptable excipient" refers to an excipient that is useful in preparing a pharmaceutical composition that is generally safe, non-toxic and neither biologically nor otherwise undesirable, and includes excipient that is acceptable for veterinary use as well as human pharmaceutical use.

"A therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

"Treating" or "treatment" of a wound includes: (1) accelerating wound healing, i.e., causing the wound to heal faster relative to an untreated wound; (2) reducing the risk of microbial infection of a wound relative to an untreated wound; and/or (3) reducing or relieving the pain associated with the wound.

"Wound" refers to any injury or condition that requires tissue generation or regeneration and is dependent on the formation of new blood vessels, or angiogenesis. A wound can be internal or external. Exemplary wounds include, but are not limited to, wound of the skin such as a cut or ulcer, gingival recession around the teeth, regeneration of nerve cells in the brain or spinal cord, and the condition of ischemia (diminished blood flow) to muscle in the heart or lower extremities. Generally, successful wound healing includes at least a partial restoration of tissue function.

Unless defined otherwise, all technical and scientific terms used herein have the meaning commonly understood by a person skilled in the art to which this invention belongs. The following references provide one of skill with a general definition of many of the terms used in this invention: Singleton et al., *Dictionary of Microbiology and Molecular Biology*, (2d ed. 1994); *The Cambridge Dictionary of Science and Technology*, (Walker ed., 1988); and Hale & Marham, *The Harper Collins Dictionary of Biology*, (1991).

Products and Processes of the Invention

Platelets, or thrombocytes, are small cytoplasmic bodies derived from cells. They circulate in the blood of mammals and are involved in hemostasis leading to the formation of blood clots. Like red blood cells, platelets have no nucleus. Platelets contain alpha and dense granules. Activated platelets excrete the contents of these granules into their canalicular systems and into surrounding blood. There are two types of granules: (i) dense granules, which contain inter alia ADP or ATP, calcium and serotonin; and (ii) α-granules, which contain inter alia platelet factor 4, PDGF, fibronectin, B-thromboglobulin, von Willebrand's factor (vWF), fibrinogen, and coagulation factors V and XIII).

The inner surface of blood vessels is lined with a thin layer of endothelial cells, that in normal hemostasis, acts to inhibit platelet activation with the production of endothelial-ADPase, noradrenaline, and $PGI_2$. Endothelial-ADPase clears away ADP, a platelet activator, from platelet surface receptors. Under the layer of endothelial cells is a layer of collagen. When the endothelial layer is injured, the collagen is exposed.

Endothelial cells produce vWF protein, a cell adhesion ligand that helps endothelial cells adhere to collagen in the basement membrane. Under typical physiological conditions, neither collagen nor vWF pass into the bloodstream. When endothelial damage occurs, platelets come into contact with exposed collagen and vWF, and the inhibitors the endothelium normally secretes are reduced. Upon contact with collagen, the platelets are activated. They are also activated by thrombin (primarily through PAR-1), ADP receptors (P2Y1 and P2Y12) expressed on platelets. Platelet activation results in the scramblase-mediated transport of negatively charged phospholipids to the platelet surface. These phospholipids provide a catalytic surface (with the charge provided by phosphatidylserine and phosphatidylethanolamine) for the tenase and prothrombinase complexes.

Platelets participate in the early phases of wound healing by binding to damaged tissue and releasing a large variety of factors that begin and sustain the healing process. Numerous factors, including VEGF, are known to be present in platelets that have a role in blood vessel formation. Isolates of growth factors from platelets have been shown to enhance the healing of wounds.

Unfortunately, most conventional platelet-derived wound healing formulae (PDWHFs) are obtained by centrifuging whole blood to obtain a plasma rich in platelets but free of red blood cells and treating the platelet rich plasma with thrombin to stimulate the production of a releasate, which can be combined with collagen. These PDWHFs typically have a limited concentration of growth factors with high concentration of albumin (e.g., 9.9%) and other serum contents. Accordingly, clinical utility of these conventional PDWHFs are limited. In addition, these PDWHFs typically contain essentially non-mature growth factors due to the use of thrombin in obtaining PDWHFs.

In contrast to compositions obtained from conventional treatment or extraction of platelets, compositions of the present invention have a significantly higher angiogenesis activity and growth activity. Furthermore, surprisingly and unexpectedly, the present inventors have found that using pelletized platelets provide a significantly improved growth factor activity and angiogenesis activity. More significantly, use of pelletized platelets significantly reduces the amount of undesired material in the composition, such as albumin, serum, plasma, etc.

Some aspects of the invention provide compositions that comprise a growth factor, platelet extract mixtures having an angiogenic activity, as well as other compositions that are useful in promoting angiogenesis or tissue regeneration, treating a wound, or a combination thereof. Various compositions of the invention are obtained by processes of the invention. Typically, processes of the invention comprise disrupting pelletized platelets in an extraction solution such that the contents of the platelets and/or the granules are released into the extraction solution. Generally the extraction solution comprises one or more of the following components, water (typically deionized water), HCl, urea, guanidine, Phosphate buffer, NaCl, $CaCl_2$, Arginine, Tris buffer, or a mixture thereof. When pelletized platelets are placed in the solution described above, in certain instances at least a portion of platelets and granules are disrupted, thereby releasing contents of platelets and granules into the solution without a need for any mechanical force. In some embodiments, pelletized platelets are further disrupted, e.g., by an external or mechanical force, to cause platelets and granules to release their contents into the extraction solution. A variety of disruption methods are known to one skilled in the art, and all such methods are within the scope of the present methods. In some particular embodiments, platelets and granules are further disrupted by sonication, homogenization, nitrogen cavitation, a French pressure cell, or a combination thereof.

In some embodiments, the solution comprises a chaotropic agent. Without being bound by any theory, it is believed that the presence of the chaotropic agent has the benefit of inactivating or destroying the lysosomal proteases that are present in the platelets, which could otherwise lead to the degradation of the desired product in the absence of the chaotropic agent. Deionized water in certain instances can act as the chaotropic agent. Other exemplary chaotropic agents include urea, guanidine, as well as those known to one skilled in the art. In some instances, the chaotropic agent is urea. In such instances, the concentration of urea used is typically about 4 M or higher, often about 6 M or higher, and more often about 8 M.

Processes of the invention can further include removing at least a portion of insoluble materials from the extraction solution. The insoluble materials are produced by disruption of the pelletized platelets and granules and comprises membrane fragments and/or other insoluble higher molecular weight proteins. Any of the known separation methods can be used to remove insoluble materials from the solution. For example, insoluble materials can be separated by centrifugation followed by collection of the supernatant, or the insoluble materials can be removed simply by filtration.

Processes of the invention can further include removing proteins having molecular weight of about 2 kD or less. Such proteins can be removed along with the insoluble materials, for example, using an ultrafiltration process. Alternatively, the insoluble materials can be removed from the extraction solution prior to removing proteins having molecular weight of 2 kD or less. For example, after removing the insoluble materials the resulting extraction solution can be dialyzed using a semipermeable membrane having 2 kD or less, often 4 kD or less, and more often 10 kD or less MWCO. Without being bound by any theory, it is believed that dialysis removes various proteins that may interfere with the tissue regeneration, tissue growth, or angiogenic activity of the platelet extract. While it is possible that some of the desired materials (e.g., materials having angiogenic activity, growth factors, etc.) may also be removed in the process of removing low molecular weight proteins, the net result is a composition having an increased tissue growth, tissue regeneration, and/or angiogenic activity. It is believed that in some instances the increased activity is a result of removing materials that may have inhibitory activity or simply that materials that bind to growth factors or angiogenic materials are removed from the extract, thus reducing the amount of antagonists. It has been found by the present inventor that dialysis against an acidic solution, often a dilute acidic solution such as 10 mM HCl solution, provides platelet extracts with a significantly increased growth and/or angiogenic activities.

In some embodiments, processes of the invention also include subjecting the extraction solution to an ultrafiltration process to remove any microorganisms, such as virus and/or bacteria, that maybe present. When a relatively long term storage of the composition is desired, it is often advantageous to store such a composition in a solid form, which reduces the likely hood of contamination or increases the stability of the composition. A solid form of the compositions of the invention can be obtained by any of the known processes, for example, by lyophilization. Lyophilization may also take place with the presence of sucrose, trehalose or other compounds to maintain biologic activity of the proteins or other additive as is commonly practiced in the art of lyophilization. Platelet extract preparations or pharmaceutical compositions comprising the same can be frozen and subsequently thawed or lyophilized and reconstituted/re-dissolved, for example with an extraction solution as defined herein. Such reconstituted solution can be used with or without dialysis against dilute acid or acidification.

Without being bound by any theory, platelet extract compositions of the invention are believed to include various growth and/or angiogenesis factors including, but not limited to VEGF, TGF-β1, TGF-β2, PDGF-BB, EGF, or a mixture thereof.

In some embodiments, compositions of the invention can include a small amount of albumin content. Generally the amount of albumin in products of the invention is about 1% or less, often about 0.7% or less, and more often about 0.4% or less. In general, compositions of the invention have a higher content of one or more wound healing or angiogenic substances (e.g., growth factors, fibronectin, thrombospondin, etc.) than platelet extract products obtained from any conventional process. Accordingly, compositions of the invention typically have a higher wound healing or tissue regeneration activity compared to platelet extract products of conventional processes.

The source of platelets is not important as compositions of the invention can be obtained from even what is known in the art as expired human platelets. Typically, apheresed platelets maintain their viablility for transfusion for about six days. After six days, these apheresed platelets are considered expired because of the risk of culturing infection causing bacteria.

In one particular embodiment of the invention, processes of the invention provide a mixture of proteins or materials that are known to aid in wound healing or tissue regeneration. In this particular embodiment, processes of the invention include centrifuging platelets and removing the serum supernatant to obtain pelletized platelets, resuspending pelletized platelets in a solution such as, but not limited to, PBS or 10 mM HCl solution or a solution comprising a chaotropic agent. The resuspended materials are subjected to conditions to destroy the membranes, for example, lysing by sonication to destroy the membranes of the platelets and granules. In some cases, the resulting supernatant after lysing and centrifugation is acidified to about pH 4 or less, typically about pH 3 or less, and more often about pH 2 or less. In one particular embodiment, the supernatant is acidified to about pH 2.

As stated above, a chaotropic agent, such as urea, can be included in the initial extraction solution. Without being bound by any theory, it is believed that the presence of the chaotropic agent has the benefit of inactivating or destroying the lysosomal proteases that are present in the platelets, which could otherwise lead to the degradation of the product in the absence of the chaotropic agent.

The acidified mixture is dialyzed against 10 mM HCl solution using a 7-8 kD membrane. The resulting material is lyophilized for storage and resolubilized in a chaotropic agent prior to its use. Exemplary chaotropic agents include urea, guanidine, as well as those known to one skilled in the art. In one particular embodiment, the chaotropic agent is urea. In such embodiment the concentration of urea is typically about 4 M or higher, often about 6 M or higher, and more often about 8 M. The reconstituted solution is then dialyzed against 10 mM HCl to remove the chaotropic agent (e.g., urea). Without being bound by any theory, it is believed that acidification and chaotropic agent (e.g., urea) solubilization activates latent forms of TGF-β super family members such as TGF-βs and BMPs. Another method of activating TGB-β super family members includes heat treatment.

Compared to platelet extract products of conventional processes, products of the invention have superior therapeutic utility in the treatment of conditions known to result from insufficient angiogenesis such as impaired wound healing, and myocardial and peripheral vascular ischemia.

Other methods for isolating or extracting materials from platelets include, but are not limited to, subcellular fractionation of the platelets by a process such as nitrogen cavitation or the use of a French pressure cell. In some instances, density centrifugation on the lysis product yields a system of bands that allow one to isolate the α-granules which are the organelles that comprise the factors that show wound healing properties. In some instances, the isolated α-granules are further subjected to processes of the invention, e.g., chaotropic agent (e.g., urea) treatment.

Other aspects of the invention include compositions comprising a therapeutically effective amount of a product of the invention and a pharmaceutically acceptable carrier, and methods for using the product or the composition of the invention.

Utility

The dynamic process of wound healing is a well regulated sequence of events which, under normal circumstances, results in the successful repair of injured tissues. First, a cutaneous wound that cuts through the epidermis and dermis (full thickness), is accompanied by blood vessel rupture. Rapidly, clot formation occurs providing a provisional matrix to cover the wound. The clot is one of the key components because it provides mechanical closure with fibrin and other matrix proteins, and it is the initial source of cytokines, growth factors and chemotactic agents released by platelet degranulation. This cocktail initiates the process of wound healing. Next, neutrophils move into the interstitum at the site of injury in response to bacterial products and other chemotactic agents. This is followed by macrophages that release chemical signals to attract fibroblasts. The resident and infiltrating fibroblasts secrete cytokines such as PDFG-BB and bFGF and begin to deposit a new extracellular matrix that will be an essential component of the scar tissue. Meanwhile, the process of reepithelialization begins on the borders of the wound where keratinocytes of the basal layer display new integrins to attach to a provisional matrix. The epidermal migration continues until a monolayer of keratinocytes covers the wound. Several known growth factors intervene in the reepithelialization of the skin (e.g., EGF, TGFa and KGF 1 and 2).

In the underlying dermis, the process of neovascularization is established in response to severed vessels and angiogenic factors produced locally. The role of the microvasculature in wound healing is essential for the repair to take place. After the interruption in the continuity of the microvasculature, endothelial cells need to dissolve their cell-cell attachments, migrate outside the vessel into the extracellular matrix, undergo mitosis and finally reassociate in an orderly manner to form a network of capillaries necessary for the healing to proceed. It appears that VEGF secreted acutely by the keratinocytes is responsible in great part for the angiogenic response. Other angiogenic factors like basic fibroblast growth factor (bFGF) and transforming growth factor b (TGFb) are also present.

Normal healing involves proliferation, migration, matrix synthesis and angiogenesis. An impairment at any of these complex phases often will lead to complications in wound healing. In diseases of impaired neovascularization, such as diabetes, dermal wound healing is severely compromised. This often leads to nonhealing wounds and, ultimately, amputation. Compositions of the invention stimulate and/or augment angiogenesis and can be of great value in diabetes and other clinical situations where healing is impaired.

Compositions of the invention promote wound healing or tissue regeneration and can be used to treat external or internal wounds. Furthermore, compositions of the invention can be used topically or systemically. Generally any type of external or internal wound can be treated with compositions of the invention to promote or facilitate wound healing. For example, compositions of the invention can be used in treating cutaneous and surface wounds. Exemplary uses include treating simple cuts and scratches, surgical wounds to decrease scar tissue formation (e.g., in the form of a bandage), treating dental and internal wounds such as in surgical applications, dental graft healing, battlefield wound treatment, treatment of myocardial infarction and other internal ischemic events. Compositions of the invention can also be used in dental and oral and maxillofacial applications, including, without limitation, bone grafting, guided tissue regeneration, involving, without limitation, the maxillo (upper jaw) or mandible (lower jaw), tissue regeneration, mucogingival surgery, perioplastic surgery, and other regenerative products including, without limitation, the oral mucosa. Other applications for the compositions of the invention include orthopedic applications (such as in ligament to bone and tendon to bone attachments), joint replacement applications (e.g., shoulders, knees, hip, etc.), treating diseased or damaged cells in cardiovascular system, treating burns, mucosal cell regeneration (e.g., in trachea, gynecology, proctology, etc.), and in general for healing various internal and external wounds.

Compositions of the invention can also be combined with other materials. For example, they can be combined with Laminin purified from placenta as a wound healant or scar minimizer. They can also be combined with Biobrane® or some other wound covering for burns and graft site regeneration. Compositions of the invention can also be loaded onto a collagen sponge to enhance tendon to bone healing when sandwiched or placed between the tendon and bone. Furthermore, compositions of the invention in carboxymethylcellulose can be used as a wound regenerant similar to Regranex®. In some instances, compositions of the invention in dilute acid, physiological buffer, or deionized water can be applied directly to a wound bed to accelerate wound healing. Compositions of the invention can also be used as a nutrient supplement for animal serum free cell culture or primary human cell cultures. Compositions of the invention can also be used as therapeutic angiogenesis agents in the heart and lower extremities and as osteogenic agents suitable for bone regeneration.

Some particular uses for compositions of the invention include soft tissue grafting procedures involving the oral mucosa including treatment of gingival recession, increasing the amount of keratinized tissue, and increasing vertical and/or horizontal gingival tissue thickness. Other uses for compositions of the invention include promoting papilla regeneration, vestibuloplasty, and tissue regeneration around dental implants. Compositions of the invention can also be used in esophagus reconstruction, oral facial reconstruction, and to repair mucosa tissue lost due to trauma or diseases such as cancer and periodontal disease.

Other application for compositions of the invention is to stimulate periodontal regeneration including the formation of cementum, periodontal ligament, and bone when applied to the surface of root surfaces of teeth. Compositions of the invention can also be used in tympanoplasty, tonsillectomy, adenoidectomy, tumor resection and wound management, plastics and reconstruction surgery including, free tissue transfer (split thickness flaps), bone grafting, Z-Plasty (or soft tissue scar reduction), and augmentation (e.g., as micronized injectable and large particle grafting material.

In some applications, compositions of the invention can be mixed with a various polymers or membrane, for example, with a membrane composed of amnion and chorion (such as those disclosed in U.S. patent application Ser. No. 12/206, 508, which is incorporated herein by reference in its entirety), or with a simple collagen membrane. Compositions of the invention can also be combined with an amnion or collagen membrane for the treatment of chronic wounds.

In some instances, solid compositions of the invention (e.g., those that are lyophilized) are hydrated at the time of application (e.g., during surgery) using saline. The reconstituted composition is typically applied directly to the desired site, for example, to the flap prior to coronally positioning over the exposed root surface of adjunct tooth in the treatment of gingival recession. Compositions of the invention can also be used to the debrided bone and cleaned root surface in the treatment periodontal osseous defects and simulate periodontal regeneration.

As stated above, compositions of the invention can be lyophilized and hydrated at the time of use, e.g., during surgery, using saline. Such reconstituted composition can be applied to a collagen membrane. In one particular embodiment, compositions of the invention is applied to a collagen membrane that is 1.5 mm thick, where the top layer of the membrane consists of amnion tissue with epithelia-layer removed, for example, using methods disclosed in the above incorporated U.S. patent application Ser. No. 12/206,508. The hydrated membrane comprising the composition of the invention can be used as alternative to free gingival grafts to increase the zone of attached gingival tissue or to help grow new gingival tissue around the exposed surface of a dental implant.

Other applications for compositions of the invention include bone grafting applications. For example, compositions of the invention can be used in dental bone grafting procedures including ridge augmentation, sinus elevation, facial reconstruction, extraction site grafting and periodontal osseous defects, where the composition of the invention is mixed with autogenous bone, and or a bone substitute. Compositions of the invention can also be mixed with autogenous bone, and/or a bone substitute, and used in conjunction with a barrier membrane for use in guided bone regeneration.

In another particular embodiment, a solution composition of the invention is lyophilized and hydrated at the time of surgery using saline, and mixed with particulate an organic bone mineral, such as those with an average diameter range of from about 250 µm to about 420 µm, and is used to treat periodontal osseous defects.

Compositions of the invention also have applications in spine, trauma, joint reconstruction, and craniofacial procedures, for example, where compositions of the invention are mixed with autogenous bone, and/or a bone substitute. One of the objectives of spinal fusion is to eliminate the excessive vertebral motion or spinal instability by fusing adjoining vertebrae. In cases where the amount of autograft bone required exceeds availability, surgeons mix in a bone substitute product usually called a bone graft "extender" to have enough material for the procedure. As the number of "levels" (vertebras) fused increases, so does the difficulty of the procedure. There are two primary spinal fusion procedures. One is interbody fusions, which use a device that is inserted into the disc space between the vertebrae. In this procedure, the inner portion of the interbody device, which is usually hollow, is filled with bone graft material. Another often used procedure is a posterolateral intertransverse process, which typically requires a large amount of bone graft material (usually autograft) to be placed in the posterolateral portion of the spine with a goal of fusing the transverse processes together. In both fusion procedures, spinal fixation devices such as pedicle screw systems, rods and plates are typically used to help stabilize the joint. As stated, compositions of the invention can be used in various spine fusion procedures. Compositions of the invention are also useful in intertranverse fusion process where natural blood supply is provided only by the de-corticated pedicles above and below the bone graft.

In fractures bone graft materials are used to treat both fresh fractures (result of a recent injury) and non-union fractures (a fresh fracture that did not heal properly). In these procedures that require a bone graft, the material is packed into the fracture site in order to fill the void and heal the bone. In addition to the bone graft material, the fracture is typically stabilized using fracture fixation devices. Compositions of the invention mixed with a bone substitute can be used in all fractures, grade A1-C3. In simple fractures such as distal radius factures and foot and ankle fusions, compositions of the invention can shorten recovery time. In non-healing fractures or factures where the blood supply is compromised, compositions of the invention can be an effective alternative to autograft or can be used at the very least as a bone graft extender.

Following diseases and/or surgical intervention human and other animal tissues heal by replacement with a fibrotic scar tissue. Such tissue does not generally possess the functional characteristics of the original tissue. Various attempts have therefore been made to obtain a healing response characterized by regeneration, i.e., the replacement of lost tissue with a newly generated tissue functionally and morphologically similar to the original one. In defined clinical situations both natural healing responses and guided tissue regeneration procedures present several limitations which decrease the extent and predictability of the desired healing outcome. Clinical application of the concept of guided tissue regeneration in periodontics (treatment of gum diseases), implantology (replacement of lost teeth by artificial bone anchored ones), orthopedics, plastic surgery, etc. has proven to be highly effective in selected conditions characterized by a particular topographic configuration of the tissue to be regenerated. In most situations, however, results are less satisfactory both in terms of amounts of obtained regenerated tissue and their predictability. Classical explanations of this phenomenon have centered the attention upon limits arising from insufficient recruitment of specific progenitor cells.

In some aspects, the invention provides a pharmaceutical composition adapted to the use in guided tissue regeneration. In some embodiments, products, compositions and methods of the invention increase microvascular blood flow, recruit progenitor cells, increase microvascular endothelium proliferation, and/or protect tissues from ischemia and reperfusion damages. Various local delivery systems can be used. Generally, delivery systems do not negatively affect tissue (e.g., periodontal) regeneration. The delivery composition can be used in combination with or without physical barriers such as plastic or resorbable polymer films. Specific formulations and application technique are adapted to the different applications.

Compositions of the invention also reduce the risk of microbial infections. Accordingly, some aspects of the invention provide methods for reducing the risk of a microbial (e.g., bacteria, yeast, and/or fungus) infection of wounds.

Polymers of various types, in combination with compositions of the invention, are useful in the present invention and include those polymer materials that are safe for use in the oral cavity and wounds of human or a lower animal. Such polymers are known, including for example polymers and copolymers such as polylactic acid ("PLA"), polyglycolic acid ("PLG"), poly lactyl-co-glycolic acid ("PLGA"), polyaminoacids such as polyaspartame, chitosan, collagen, polyalburrin, gelatin and hydrolyzed animal protein, polyvinyl pyrrolidone xanthan and other water soluble gums, polyanhydride, and poly orthoesters.

In some embodiments, useful polymers include the copolymers comprising mixtures of lactide and glycolide monomers. Lactide monomeric species can comprise from about 15% to about 85%, often from about 35% to about 65% of the polymers, while glycolide monomeric species comprise from about 15% to about 85% of the polymer, often from about 35% to about 65% on a molar basis. However, it should be appreciated that the scope of the invention is not limited to any particular copolymer ranges disclosed or exemplified herein. The range of copolymer contents can vary according to a particular application. Generally, the molecular weight of the copolymer typically lies in the range of from about 1000 to about 120,000 (number average). These polymers are described in detail in U.S. Pat. No. 4,443,430, issued to Mattei, which is incorporated herein by reference in its entirety.

A feature of fluid gel or paste-like compositions containing certain of such copolymers is their transformation into near solid phase in the presence of aqueous fluid such as water, aqueous buffers, serum, crevicular fluid, or other body fluid. For example, when a sample of such a gel is placed into a tube containing water or human serum, the composition becomes nearly solid in the receptor phase. Without being bound by any theory, this is believed to be due to insolubility of the poly(lactyl-co-glycolide) copolymer in water, and related aqueous solvents such as may be present in wound or crevicular fluid. Thus, even though such fluid compositions can potentially be used advantageously when desired from a syringe-like apparatus, they still offer the advantages of solid devices at the treatment sites such as dental applications. Further, since such polymeric materials do undergo slow degradation via hydrolysis, the product of the invention continues to release in a sustained manner from such compositions and the composition does not need to be surgically removed following tissue regeneration.

In some embodiments of dental applications, the product of the invention generally comprises from about 1% to about 90%, often from about 10% to about 70%, of the compositions/devices useful for the methods of the invention. It should be appreciated, however, that the scope of the invention is not limited to any particular ranges given here and in the Examples. One skilled in the art can readily determine the appropriate amounts and ranges of the product of the invention depending on the particular composition, device, and/or wound to be treated.

Administration and Composition

In treating wounds, the products of the invention can be utilized in compositions such as tablets, capsules or elixirs for oral administration, suppositories for rectal administration, sterile solutions or suspensions for parenteral or intramuscular administration and the like.

The pharmaceutical compositions of the invention can be used in the form of a pharmaceutical preparation, for example, in solid, semi-solid or liquid form which comprises a product of the invention, as an active ingredient, in admixture with an organic or inorganic carrier or excipient suitable for external, enteral or parenteral applications. The active ingredient can be compounded, for example, with the usual non-toxic pharmaceutically acceptable carriers for tablets, pellets, capsules, suppositories, solutions, emulsions, suspensions, and any other form suitable for use. The carriers which can be used are water, glucose, lactose, gum acacia, gelatin, mannitol, starch paste, magnesium trisilicate, talc, corn starch, keratin, colloidal silica, potato starch, urea and other carriers suitable for use in manufacturing preparations, in solid, semisolid or liquid form and in addition auxiliary, stabilizing, thickening and coloring agents and perfumes can be used. The active product (e.g., an agent that mediates angiogenic and/or wound healing capability) is included in the pharmaceutical composition in an amount sufficient to produce the desired effect upon the process or condition (e.g., regulation of neovascularization) of the disease.

For preparing solid compositions such as tablets, the principal active ingredient is mixed with a pharmaceutical carrier (e.g., conventional tableting ingredients such as corn starch, lactose, sucrose, sorbitol, talc, stearic acid, magnesium stearate, dicalcium phosphate or gums) and other pharmaceutical diluents (e.g., water) to form a solid preformulation composition containing a substantially homogeneous mixture of a product of the invention. When referring to the preformulation compositions as substantially homogenous, it is meant that the active ingredient is dispersed evenly throughout the composition so that the composition may be readily subdivided into equally effective unit dosage forms such as tablets, pills and capsules.

The tablets or pills of the novel composition can be coated or otherwise compounded to provide a dosage form affording the advantage of prolonged action. For example, the tablet or pill can comprise an inner dosage an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings such materials including a number of polymeric acids and mixtures of polymeric acids with such materials as shellac, cetyl alcohol and cellulose acetate.

The liquid forms, in which the novel composition of the invention can be incorporated for administration orally or by injection, include aqueous solution, suitably flavored syrups, aqueous or oil suspensions, and flavored emulsions with edible oils such as cottonseed oil, sesame oil, coconut oil, or peanut oil as well as elixirs and similar pharmaceutical vehicles. Suitable dispersing or suspending agents for aqueous suspensions include synthetic natural gums, such as tragacanth, acacia, alginate, dextran, sodium carboxymethyl cellulose, methylcellulose, polyvinylpyrrolidone or gelatin.

Liquid preparations for oral administration may take the form of, for example, solutions, syrups or suspensions, or they may be presented as a dry product for reconstitution with water or other suitable vehicles before use. Such liquid preparations may be prepared by conventional means with pharmaceutically acceptable additives such as suspending agents (e.g., sorbitol syrup, methyl cellulose or hydrogenated edible fats); emulsifying agents (e.g., lecithin or acacia); non-aqueous vehicles (e.g., almond oil, oily esters or ethyl alcohol); preservatives (e.g., methyl or propyl p-hydroxybenzoates or sorbic acid); and artificial or natural colors and/or sweeteners.

For buccal administration, the composition may take the form of tablets or lozenges formulated in conventional manners.

For topical administration, formulations may be made up with a product of the invention which may be combined in admixture with at least one other ingredient constituting an acceptable carrier, diluent or excipient in order to provide a composition, such as a cream, gel, solid, paste, salve, powder, lotion, liquid, aerosol treatment, or the like, which is most suitable for topical application. Sterile distilled water alone and simple cream, ointment and gel bases may be employed as carriers of the active agents. Examples of bases and suspending vehicles include Fattibase® (acrylic polymer resin base), Polybase® (polyethylene glycol base) by Paddock Laboratories, Inc. Additional therapeutic agents may be added to the formulations as medically indicated, selected from the classes of: keratolytics, surfactants, counter-irritants, humectants, antiseptics, lubricants, astringents, wound additional healing agents, emulsifiers, wetting agents, additional adhesion/coating protectants, additional anti-inflammatory agents, vasoconstrictors, vasodilators, anticholinergics, corticosteroids (e.g., glucocorticoids) and anesthetics. Preservatives and buffers may also be added. The formulation may be applied to a sterile dressing, biodegradable, absorbable patches or dressings for topical application, or to slow release implant systems with a high initial release decaying to slow release. When the compositions are administered to treat burns, they may be in the form of an irrigant, preferably in combination with a physiological saline solution. Compositions can also be in the form of ointments or suspensions, typically in combination with purified collagen. The compositions may also be impregnated into transdermal patches, plasters, and bandages. For additional topical compositions contemplated for therapeutic administration, see U.S. Pat. Nos. 5,662,904; 5,679,655; and 5,705,477, all of which are incorporated herein by reference it their entirety.

The product of the invention can also be formulated for parenteral administration by injection, which includes using conventional catheterization techniques or infusion. Formulations for injection may be presented in unit dosage form, e.g., in ampules, or in multi-dose containers, with an added preservative. The compositions may take such forms as suspensions, solutions or emulsions in oily or aqueous vehicles, and may contain formulating agents such as suspending, stabilizing, and/or dispersing agents. Alternatively, the active ingredients may be in powder form for reconstitution with a suitable vehicle, e.g., sterile pyrogen-free water, before use.

Some aspects of the invention includes compositions comprising at least one product of the invention together with at least one pharmaceutically acceptable carrier, and optionally other therapeutic and/or prophylactic ingredients, such as antimicrobial compounds and analgesic compounds.

In general, the products of the invention are administered in a therapeutically effective amount by any of the accepted modes of administration for agents that serve similar utilities. Suitable dosage ranges are typically 0.001 mg to 1 mg daily depending upon numerous factors such as the severity of the wound to be treated, location of the wound, the age and relative health of the subject, the route and form of administration, the indication towards which the administration is directed, and the preferences and experience of the medical practitioner involved. One of ordinary skill in the art of treating wounds will be able, without undue experimentation and in reliance upon personal knowledge and the disclosure of this Application, to ascertain a therapeutically effective amount of the products of the invention for a given wound treatment.

In some aspects of the invention, products of the invention are administered as pharmaceutical formulations including those suitable for topical, oral (including buccal and sublingual), rectal, nasal, pulmonary, vaginal, or parenteral (including intramuscular, intraarterial, intrathecal, subcutaneous and intravenous) administration or in a form suitable for administration by inhalation or insufflation. Typically, the manner of administration is topical using a convenient pharmaceutical carrier such as bandages, artificial skin, polymers, and other wound dressing medium that are conventionally used. Additionally, synthetic products such as Dermagraft-TC, which is made from living human cells and it is being used instead of cadaver skin, can be used. In addition to Dermagraft-TC, artificial burn dressings can be used, e.g., in treating burns. Exemplary artificial burn dressings include Integra Artificial Skin and BioBrane. Skin substitute BioBrane is a nylon material that contains a gelatin that interacts with clotting factors in the wound. It is believed that interaction causes the dressing to adhere better, forming a more durable protective layer. Unlike traditional bandages, artificial burn dressings also promote wound healing by interacting directly with body tissues.

Integra is a two-layered dressing. The top layer serves as a temporary synthetic epidermis; the layer below serves as a foundation for re-growth of dermal tissue. The underlying layer comprises collagen fibers that act as a lattice through which the body can begin to align cells to recreate its own dermal tissue.

Other substitute skin products can also be used with products of the invention. For example, Apilgraf (Organogenesis Inc., Canada) is a living "human skin equivalent" that can be used to treat wounds and ulcers. Additionally, implantable human tissues (e.g., available from LifeCell Corp.) can be used with products of the invention in reconstructive surgery and burn treatment.

A product of the invention, together with one or more conventional adjuvants, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended wound healing. The pharmaceutical compositions can be employed as gels, ointments, solids (as a part of wound dressing material such as bandages, artificial skins, casts, polymeric mixtures, semisolids, powders, and/or sustained release formulations), or liquids such as solutions, suspensions, emulsions, or elixirs; or in the form of suppositories for rectal or vaginal administration.

The products of the invention can be formulated in a wide variety of materials for surgical placement forms. The pharmaceutical compositions and dosage forms can comprise a product of the present invention as the active component.

The pharmaceutically acceptable carriers can be either solid, gel, or liquid. Solid pharmaceutically acceptable carriers include, but are not limited to, polymers (e.g., for placing the products of the invention at a desirable site such as spine, vertebrae, tooth, nerve cells, cardiovascular organs, digestive organs, or any other internal organs), bandages (including fabric and polymers), artificial skins, sutures, etc.

Other forms suitable for wound healing include gel or ointment form preparations including emulsions, syrups, elixirs, aqueous solutions, aqueous suspensions, or solid form preparations that are intended to be converted shortly before use to gel or liquid form preparations. Emulsions can be prepared in solutions, for example, in aqueous propylene glycol solutions or may contain emulsifying agents, for example, such as lecithin, sorbitan monooleate, or acacia. Aqueous solutions can be prepared by dissolving the products of the invention in water and adding suitable colorants, stabilizers, and thickening agents. Aqueous suspensions can be prepared by dispersing the finely divided products of the invention in water with viscous material, such as natural or synthetic gums, resins, methylcellulose, sodium carboxymethylcellulose, and other well known suspending agents. Solid form preparations include solutions, suspensions, and emulsions, and may contain, in addition to the active component, colorants, stabilizers, buffers, dispersants, thickeners, solubilizing agents, and the like.

The compounds of the invention also can be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents.

The products of the invention can be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the invention can be formulated for vaginal administration. Pessaries, tampons, creams, gels, pastes, foams or sprays containing in addition to the active ingredient such carriers as are known in the art to be appropriate.

The compounds of the invention can also be formulated for nasal administration. The solutions or suspensions are applied directly to the nasal cavity by conventional means, for example, with a dropper, pipette or spray. The formulations may be provided in a single or multidose form. In the latter case of a dropper or pipette, this can be achieved by the patient administering an appropriate, predetermined volume of the solution or suspension. In the case of a spray, this can be achieved for example by means of a metering atomizing spray pump.

The products of the invention also can be formulated for aerosol administration, particularly to the respiratory tract and including intranasal administration. The products will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatin or blister packs from which the powder may be administered by means of an inhaler.

When desired, formulations can be prepared for sustained or controlled release administration of the products of the invention. For example, the products of the invention can be formulated in transdermal or subcutaneous delivery devices. These delivery systems are advantageous when sustained release of the product of the invention is desired or necessary. Products in transdermal delivery systems are frequently attached to an skin-adhesive solid support. The compound of interest can also be combined with a penetration enhancer, e.g., Azone (1-dodecylazacycloheptan-2-one). Sustained release delivery systems can be inserted subcutaneously into the target organ or subdermal layer by surgery or injection. In some instances, the subdermal implants encapsulate the product of the invention in a lipid soluble membrane, e.g., silicone rubber, or a biodegradable polymer, e.g., polylactic acid.

Additional objects, advantages, and novel features of this invention will become apparent to those skilled in the art upon examination of the following examples thereof, which are not intended to be limiting. In the Examples, procedures that are constructively reduced to practice are described in the present tense, and procedures that have been carried out in the laboratory are set forth in the past tense.

EXAMPLES

Example 1

The human platelet morphogen (HPM) material was made by transferring the unit of platelets into 50 mL centrifuge tubes (about 4-6 tubes) and centrifuging at about 3500-4800 rpm to produce platelet pellets. The supernatant serum/media was removed using a pipette. A total of 60 mL of cold 10 mM HCl solution, PBS, or 6-8 M urea with or without 5 mM $CaCl_2$ was used to resuspend the platelet pellets which were then kept on ice during the process of sonication using a Branson Sonifier 450 (Branson Ultrasonics Corporation, Village of Lakewood, Ill.) with Duty cycle set to 20% and output control set to 2. Sonication was conducted for 4 minutes with the probe tip placed in the liquid phase during the process. The resulting solutions were placed in a high G centrifuge for 40 minutes to 1.5 hours. The resulting supernatants were collected and dialyzed in a 7-8 KD MWCO bag (5 1 1 exchanges lasting at least 6 hours each) against cold 10 mM HCl solution to remove urea or buffer and salts.

Bradford assays were done that yielded around 3-5 mg/mL (for the entire 60 mL used) when lysis was done in dilute HCl or PBS and 7-8 mg/mL when done in urea. All Matrigel plug assays were done with defined doses based on these concentrations. In some instances, this material was lyophilized and the weight of this product was measured yielding a weight approximately 10% greater than that determined by the Bradford assay.

Example 2

A unit of expired platelets was obtained from the blood bank and the entire composition was distributed into 8×50 mL centrifuge tubes. These tubes were spun at 4000 rpm for 15 minutes and the supernatant was carefully removed to yield a pellet of platelets at the bottom of each tube. A 10 mL of solution composed of 6 M urea in 10 mM Tris pH 6.7 buffer solution was placed in each tube and a clean pipette tip was used to dissaggregate each pellet followed by brief vortexing (3-5 seconds) to further resuspend the pellet. Each tube was treated for two minutes by submerging a sonicator probe into the solution and activating the sonication for 30 seconds. The resulting solutions were loaded into 30 mL centrifuge tubes and spun at 17000 rpm for 45 minutes. The resulting supernatants were collected with a pipette and loaded into dialysis bags with a 3.5 kD pore size and placed into one liter containers of chilled (about 4° C.) 10 mM HCl solution. Over a three day period these solutions were exchanged 4 times after a minimum of 8 hours with 1 liter of fresh chilled 10 mM HCl solution. The solutions were then removed from the bags and stored in 15 mL centrifuge tubes in a refrigerator.

This resulted in a solution with a protein concentration by Bradford assay of about 5.5 mg/mL. A total of 18.9 μL of this cold solution was loaded into 1 mL of chilled, liquid Growth Factor Reduced Matrigel (Becton-Dickinson). This solution was injected in five ICR mice using a 1 mL 27 g syringe under the skin of the lower abdomen in approximately 200 μL aliquots to form a distinct plug in 5 ICR mice. Another 1 mL of chilled liquid GFR Matrigel was loaded with 37 μL of 10 mM HCl solution and injected in another 5 ICR mice under the skin of the lower abdomen in approximately 200 μL aliquots to form a distinct plug in each. This served as the control group. After seven days the animals were sacrificed and the plugs and surrounding tissue were carefully dissected and prepared for histological examination by formalin fixation. Each plug was processed as follows; the plugs and surrounding tissues were bisected approximately through the middle into equal halves, each half was placed in a separate paraffin block, each block was sectioned at two levels, offset typically by 100 μm, then each section was H&E stained, and then mounted for viewing in a microscope. At a 40×-400× magnification, functional capillaries that had been identified and defined by the presence of red blood cells within a lumen surrounded by endothelial cells within the plugs at least a distance of 50 microns from a tissue edge within the plug were counted over the entirety of the plug in each half section at two levels of each half. A count was done for each of the two sections from each plug and the total count over all plugs from each group of five animals was tallied. The group injected with plugs loaded with 37 μL of 10 mM HCl solution showed no (0) capillaries. The group injected with plugs containing the 18.9 μL of cold platelet material solution had a total of 66 functional capillaries. See FIGS. 1A and 1B for pictures of sections with and without the composition of the invention, respectively. In FIG. 1A, a scant infiltration of formation of tubes cells is seen along the perimeter of the Matrigel plug, but not throughout the volume. No fully formed capillaries are present indicating poor angiogenic activity. In FIG. 1B, dramatic abundance of capillary and tubular forms that infiltrate the entire cross-section of the plug can be seen. A higher magnification view (not shown) showed an active capillary containing 10 red blood cells. This image shows the powerful angiogenic properties of the compositions of the invention.

Example 3

Figure 2:
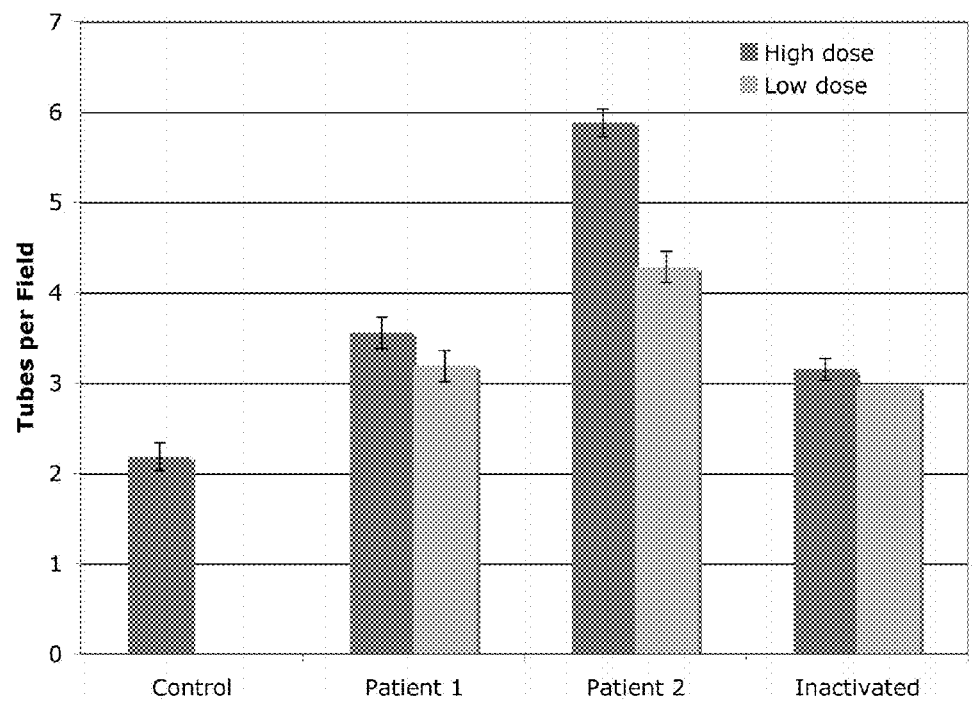
FIG. 2 is a graph showing counts of tubes/field within Matrigel plugs placed subcutaneously in mice for two units of platelets obtained from different patients processed by sonication in physiologic media followed by dialysis against 10 mM HCl followed by lyophilization and resolubilization in concentrated urea and then dialysis again against 10 mM HCl.
Figure 3:
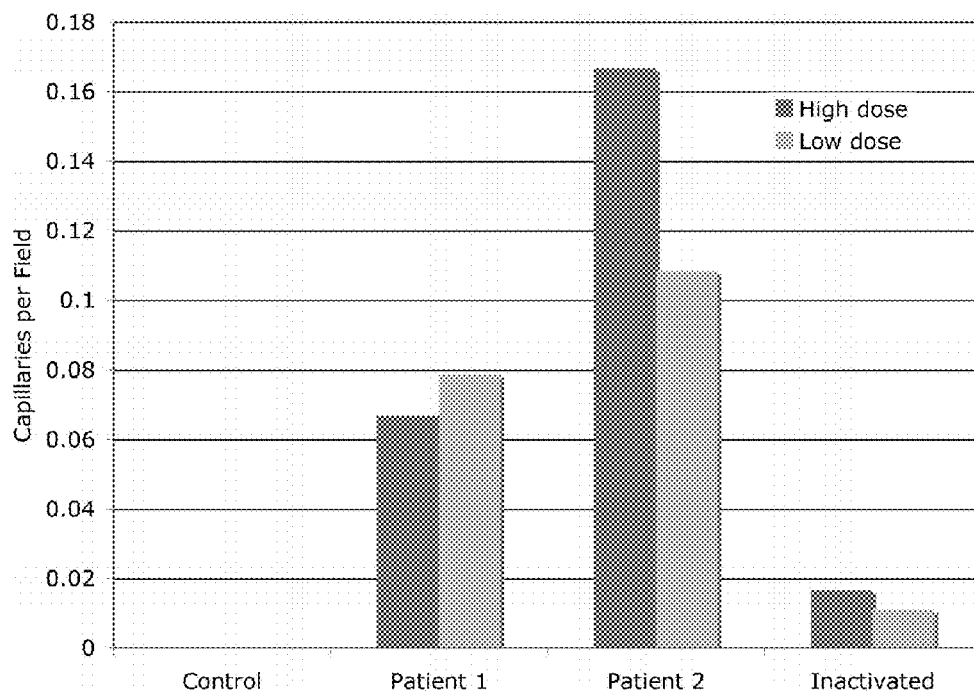
FIG. 3 is a bar graph showing the corresponding counts of capillaries/field of FIG. 2.

The Matrigel plugs containing the heat treated product of the invention or the acidified and urea treated product of the invention is placed subcutaneously in mice and examined histologically after seven days. Matrigel plugs comprising acidification and urea treated products of the invention resulted in induction of a larger number of tubes and functional capillaries containing red blood cells than a fraction that was only treated by suspension in PBS, sonication, and ultracentrifugation. This effect demonstrated a dose dependence and an angiogenic response in vivo (FIGS. 2 and 3).

Example 4

A unit of expired platelets was obtained from the Bonfils blood bank and aliquoted into 50 mL centrifuge tubes which were spun at 3600 rpm for 15 minutes. The supernatant fluid was pipetted from each of the pellets carefully to avoid its disturbance. The pellets were resuspended in 14 mL of 10 mM HCl in water and each solution was processed by placing the probe of a Branson 450 sonifier into the solutions while contained in an ice bucket and run for 4 minutes at duty cycle setting 20% and output control 2. The material was then loaded into high speed centrifuge tubes and centrifuged at 25,000 rpm for 45 minutes and the supernatant solution was removed from the pellets. One portion of these solutions was placed into a 7-8 kD MWCO dialysis bag and exhaustively dialyzed against 4 1 L volumes of 10 mM HCl at refrigerated temperature. This material was protein assayed using the Bradford technique and showed a concentration of 17.4 mg/mL.

A second portion was not dialyzed but instead treated with additional concentrated HCl to reach a pH of 2 and this material was Bradford assayed yielding a protein concentration of 21.0 mg/mL, suggesting that a portion of the protein material lost in the dialysis step for the first portion remained in this second portion.

Volumes of 3 and 10 µL of each of these materials as well as enough additional 10 mM HCl to make a total combined loading volume of 45 µL were then loaded while cold into four 1300 µL portions of liquid Matrigel and injected subcutaneously on bilateral lower abdominal sites in 3 mice to yield a total of 6 plugs for each treatment. Another equal portion of Matrigel was loaded with 45 µL of 10 mM HCl and injected as six plugs in three mice to act as a control. This dosing suggests that approximately 10-15% more protein material was loaded into the Matrigel plugs for the nondialyzed treatment. After seven days the mice were euthanized, the plugs and surrounding tissues were harvested, formalin fixed overnight, sectioned in half down the approximate midline and prepared for histological sections to be taken and made from each half The resulting twelve H&E stained sections (not shown) from each treatment and control group (3 mice, 2 plugs each, 2 halves per plug) were exhaustively viewed under a microscope at magnifications up to 400× to identify all capillaries present within the plug at least 50 microns from a preexisting tissue boundary that contained red blood cells and distinct architecture defined by an encircling endothelial cell. The dialyzed portion gave a total of 5 and 12 capillaries for the low and high doses, respectively. The nondialyzed portion gave 1 and 6 capillaries for the low and high doses, respectively. The control group showed no capillaries within the plugs.

This demonstrates an angiogenic activity in the plugs proportionate to the dose of material loaded into the Matrigel and that the process of dialysis led to an enhancement of this activity relative to the undialyzed portion. This also suggests that the low molecular weight protein that was removed by dialysis has an antiangiogenic activity. Any process that allows for the removal of these low molecular weigh proteins, such as any type of filtration, would be expected to lead to the same level of enhancement of angiogenic activity in the left over material.

Example 5

After anesthetizing the mouse by IP injection the lower back was shaved, wiped with an antiseptic wipe, allowed to dry, and a one cm full-thickness incision running perpendicular to the spinal axis was made in the skin using a sterile scissors on a pinched up portion of skin. A small aliquot of Matrigel (25 µL) either with or without added composition of the invention was placed in the wound followed by the placement of a single suture to re-approximate the edges. Animals were placed in cages alone to prevent disruption of the wound by fellow cage mates. The animals were checked after one hour for any signs of adverse events. The animals were checked daily to observe the progress of wound closure and after 3 days an image of the wound site was collected for analysis.

Figure 4:
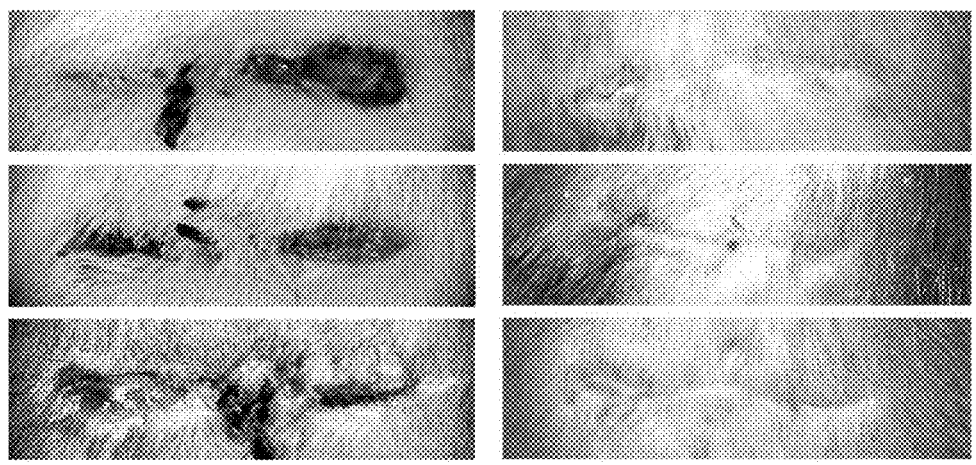
FIG. 4 is a picture showing the result of wound healing in mice with and without the composition of the invention.

FIG. 4 shows pictures of mice treated with and without a product of the invention. This experiment used the material obtained from patient 2 described below. As can be seen, mice treated with products of the invention showed better and/or faster wound healing compared to the mice in the control group.

Matrigel Plug Method for Determining Angiogenic Activity

After anesthetizing the mouse by IP injection the lower abdomen is shaved and an aliquot of 200 µL of Matrigel, diluted by no more than 10% by the solution containing growth factors, either without (control) or with added growth factors is placed subcutaneously in the right and left lower abdomenal quadrants of mice. Animals were sacrificed 7 days later for tissue harvest. Excised plugs and surrounding tissue was fixed in 10% neutral buffered formalin over night and then sectioned in half down the middle of the plugs and subsequently processed for imbedding in paraffin. Seven (7) micron sections were stained with hematoxylin and eosin and viewed through a microscope. Counts of tubular forms and functional red blood cell-filled capillaries were done within the plugs for the 10 high power fields (400×) that displayed the highest number of these forms over the entire plug. The area within 50 microns of the plug boundary with the native tissue was excluded from this determination to exclude vessels that were likely epreexisting before plug placement.

FIG. 2 shows counts of tubes/field within Matrigel plugs placed subcutaneously in mice for two units of platelets obtained from different patients processed by sonication in physiologic media followed by dialysis against 10 mM HCl followed by lyophilization and resolubilization in concentrated urea and then dialysis again against 10 mM HCl. The inactive material is a portion of that from patient 1 which has been lysed in physiologic media but not taken through any subsequent processing steps. The control condition involves loading the Matrigel with vehicle without platelet growth factors, in this case 10 mM HCl solution. The doses, in nanograms/microliter were as follows: patient 1, high=67, low 22;

patient 2, high=94, low=31; patient 1 inactive, high=143, low=48. FIG. 3 shows the corresponding counts of capillaries/field.

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those skilled in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A method for regenerating a tissue or treating a wound in a subject, said method comprising contacting a desired site for tissue regeneration or the wound in a subject with a composition comprising a growth factor, wherein said composition is produced by a process comprising:
    disrupting pelletized platelets in an extraction solution to produce an insoluble material portion and the extraction solution comprising a growth factor; and
    removing insoluble materials and proteins having molecular weight of 2 kD or less from said extraction solution to produce a composition comprising a growth factor.

2. The method of claim 1, wherein said process further comprises subjecting said extraction solution to an ultrafiltration process to remove any microorganisms that maybe present.

3. The method of claim 2, wherein said process further comprises lyophilizing said extraction solution to produce a solid composition comprising the growth factor.

4. The method of claim 3, wherein said process further comprises dissolving said solid composition in a solution to produce a fluid composition comprising the growth factor.

5. The method of claim 1, wherein said growth factor comprises VEGF, TGF-β1, TGF-β2, PDGF-BB, EGF, or a mixture thereof.

6. The method of claim 1, wherein the desired site for tissue regeneration comprises a burn site, a graft donor site, an oral and maxillofacial surgery site, a mucogingival surgery site, a perioplastic surgery site, an oral mucosa site, or a combination thereof.

7. A method for reducing a risk of microbial infection in a wound area of a subject, said method comprising treating the wound area of a subject with a wound treatment composition produced by a process comprising:
    disrupting pelletized platelets in a solution to produce an insoluble material portion and an extraction solution; and
    removing insoluble materials and proteins having molecular weight of 2 kD or less from said extraction solution to produce a wound treatment composition.

8. The method of claim 7, wherein said process further comprises subjecting said extraction solution to an ultrafiltration process to remove any microorganisms that maybe present.

9. The method of claim 8, wherein said process further comprises lyophilizing said extraction solution to produce a solid wound treatment composition.

10. The method of claim 9, wherein said process further comprises dissolving said solid wound treatment composition in a solution to produce a solution of wound treatment composition.

* * * * *